US008349575B2

(12) United States Patent
McKenzie et al.

(10) Patent No.: US 8,349,575 B2
(45) Date of Patent: Jan. 8, 2013

(54) RELAY VACCINE

(75) Inventors: Brent Steven McKenzie, Upwey (AU); Jefferey Stephen Boyle, Heidelberg (AU); Andrew Mark Lew, Essendon (AU)

(73) Assignee: The Council of the Queensland Institute of Medical Research (QIMR), Herston, Queensland (AU)

( * ) Notice: Subject to any disclaimer, the term of this patent is extended or adjusted under 35 U.S.C. 154(b) by 13 days.

(21) Appl. No.: 13/029,884

(22) Filed: Feb. 17, 2011

(65) Prior Publication Data
US 2011/0165181 A1 Jul. 7, 2011

Related U.S. Application Data

(63) Continuation of application No. 11/004,961, filed on Dec. 7, 2004, now abandoned.

(51) Int. Cl.
G01N 33/00 (2006.01)
G01N 33/53 (2006.01)
G01N 33/567 (2006.01)
(52) U.S. Cl. ........ 435/7.24; 435/7.1; 435/7.21; 514/837
(58) Field of Classification Search ................ 435/7.24, 435/7.21, 7.1; 514/837
See application file for complete search history.

(56) References Cited

U.S. PATENT DOCUMENTS

| | | | |
|---|---|---|---|
| 5,939,400 A | 8/1999 | Steinman et al. | |
| 6,110,898 A | 8/2000 | Malone et al. | |
| 6,485,726 B1 | 11/2002 | Blumberg et al. | 424/178.1 |
| 6,815,414 B2 * | 11/2004 | Chowers et al. | 514/12.3 |
| 2004/0023373 A1 | 2/2004 | Briskin | 435/320.1 |
| 2005/0187152 A1 * | 8/2005 | Gevas et al. | 514/12 |

FOREIGN PATENT DOCUMENTS

| | | |
|---|---|---|
| WO | WO93/19183 | 9/1993 |
| WO | WO94/13312 | 6/1994 |
| WO | WO95/20660 | 8/1995 |
| WO | WO99/43839 | 9/1999 |

OTHER PUBLICATIONS

Hamann et al 1994 Journal of Immunology 1994 152 pgs. 3282-3293.*
Eisenbraun, et al., "Examination of Parameters Affecting the Elicitation of Humoral Immune Responses by Particle Bombardment-Mediated Genetic Immunization," DNA Cell. Biol. (1993) 12; 791-797.
Lee & Lee, "Conjugation of Glycopeptides to Proteins," Methods Enzymol. (1989) 179: 253-7.
Marriott & Ottl, "Synthesis and Applications of Heterobifunctional Photocleavable Cross-Linking Reagents," Methods Enzymol. (1998) 291:155-75.
Montgomery, et al., "Heterologous and Homologous Protection Against Influenza A by DNA Vaccination: Optimization of DNA Vectors," DNA Cell. Biol. (1993) 12: 777-783.
Owens & Young, "The Genetic Engineering of Monoclonal Antibodies," J. Immunol. Meth. (1994) 168: 149-165.
Stott, et al., "Candidate Vaccines Protect Macaques Against Primate Immunodeficiency Viruses," AIDS Res. Hum. Retroviruses (Oct. 1998) 14 Suppl. 3: S-265-70.
Westerlund-Wikstrom, "Peptide Display on Bacterial Flagella: Principles and Applications," Int. J. Med. Microbiol. (2000) 290: 223-30.
Steinman & Cohn "Identification of a Novel Cell Type in Peripheral Lymphoid Organs of Mice," J. Exp. Med. (1973) 137(5): 1142-62.
Wu, et al., "Thymic Dendritic Cell Precursors: Relationship to the T Lymphocyte Lineage and Phenotype of the Dendritic Cell Progeny," J. Exp. Med (1996) 184(3): 903-11.
Reiter & Pastan, "Antibody Engineering of Recombinant Fv hnmunotoxins for Improved Targeting of Cancer: Disulfide-stabilized Fv Immunotoxins," Clin. Cancer Res. (1996) 2: 245-52.
Frey & Neutra, "Targeting of Mucosal Vaccines to Peyer's Patch M Cells," Behring Inst. Mitt. (1997) 98: 376-89.
Andrew, D.P., et al., "Distinct but Overlapping Epitopes Are Involved in $\alpha_4\beta_7$-Mediated Adhesion to Vascular Cell Adhesion Molecule-1, Mucosal Addressin-1, Fibronectin, and Lymphocyte Aggregation," J. of Immunol. 1994; 153(9):3847-3861.
Andrew, D.P., et al., "Distribution of $\alpha_4\beta_7$ and $\alpha_E\beta_7$ integrins on thymocytes, intestinal epithelial lymphocytes and peripheral lymphocytes," Eur. J. Immunol. 1996; 26:897-905.
Anjuère, F., et al., "Definition of Dendritic Cell Subpopulations Present in the Spleen, Peyer's Patches, Lymph Nodes, and Skin of the Mouse," Blood 1999; 93(2):590-598.
Asselin-Paturel, C., et al., "Mouse type I IFN-producing cells are immature APCs with plasmacytoid morphology," Nature Immunology 2001; 2(12):1144-1149.
Balázs, M., et al., "Blood Dendritic Cells Interact with Splenic Marginal Zone B Cells to Initiate T-Independent Immune Responses," Immunity 2002; 17:341-352.
Belz, G.T., et al., "Cutting Edge: Conventional $CD8\alpha^+$ Dendritic Cells Are Generally Involved in Priming CTL Immunity to Viruses," J. of Immunol. 2004: 172:1996-2000.

(Continued)

Primary Examiner — Gary Nickol
Assistant Examiner — Nina Archie
(74) Attorney, Agent, or Firm — Karl Bozicevic; Bozicevic, Field & Francis LLP

(57) ABSTRACT

The present invention provides a method and composition for raising an immune response in an animal. The method comprising administering to the animal a composition comprising a carrier and an antigen bound to a targeting moiety. The targeting moiety binds to at least one receptor that is upregulated on lymphocytes that home to $MAdCAM^+$ mucosal lymphoid tissues.

3 Claims, 5 Drawing Sheets

OTHER PUBLICATIONS

Berlin, C., et al., "α4β7 Integrin Mediates Lymphocyte Binding to the Mucosal Vascular Addressin MAdCAM-1," Cell 1993; 74:185-195.

Boonstra, A., et al., "Flexibility of Mouse Classical and Plasmacytoid-derived Dendritic Cells in Directing T Helper Type 1 and 2 Cell Development: Dependency on Antigen Dose and Differential Toll-like Receptor Ligation," J. Exp. Med. 2003; 197(1):101-109.

Boyle, J.S., et al., "Enhanced responses to a DNA vaccine encoding a fusion antigen that is directed to sites of immune induction," Nature 1998; 392:408-411.

Brandtzaeg, P., et al., "Regional specialization in the mucosal immune system: primed cells do not always home along the same track," Immunol. Today 1999; 20(6):267-277.

Carayanniotis, G., et al., "Adjuvant-free IgG responses induced with antigen coupled to antibodies against class II MHC," Nature 1987;327: 59-61.

Cepek, K.L., et al., "Adhesion between epithelial cells and T lymphocytes mediated by E-cadherin and the $\alpha^E\beta_7$ integrin," Nature 1994; 372:190-193.

Denis, O., et al., "Resting B cells can act as antigen presenting cells in vivo and induce antibody responses," International Immunol. 1993; 5(1):71-78.

Erle, D.J., et al., "Expression and Function of the MAdCAM-1 Receptor, Integrin α4β7 on Human Leukocytes," J. of Immunol. 1994; 153:517-527.

den Haan, J.M.M., et al., "CD8+ but Not CD8− Dendritic Cells Cross-prime Cytotoxic T Cells in Vivo," J. Exp. Med. 2000; 192(12):1685-1695.

Farstad, I.N., et al., "Distribution of β7 integrins in human intestinal mucosa and organized gut-associated lymphoid tissue," Immunology 1996; 89:227-237.

Foster, N., et al., "*Ulex europaeus* 1 lectin targets microspheres to mouse Peyer's patch M-cells in vivo," Vaccine 1998; 16(5):536-541.

García de Vinuesa, C., et al., "Dendritic cells associated with plasmablast survival," Eur. J. Immunol. 1999; 29:3712-3721.

Grewel, H.M.S., et al., "Measurement of specific IgA in faecal extracts and intestinal lavage fluid for monitoring of mucosal immune responses," J. of Immunol. Methods 2000; 239:53-62.

Hamann, A., et al., "Role of $\alpha_4$-Integrins in Lymphocyte Homing to Mucosal Tissues in Vivo," J. of Immunol. 1994; 152:3282-3293.

Harshyne, L.A., et al., "Dendritic Cells Acquire Antigens from Live Cells for Cross-Presentation to CTL," J. of Immunol. 2001; 166:3717-3723.

Hawiger, D., et al., "Dendritic Cells Induce Peripheral T Cell Unresponsiveness Under Steady State Conditions In Vivo," J. Exp. Med. 2001; 194(6): 769-779.

Heijnen, I.A.F.M., et al., "Antigen Targeting to Myeloid-specific Human FcγRI/CD64 Triggers Enhanced Antibody Responses in Transgenic Mice," J. Clin. Invest. 1996; 97(2): 331-338.

Hochrein, H., et al., "Differential Production of IL-12, IFN-α, and IFN-γ by Mouse Dendritic Cell Subsets," J. of Immunol. 2001; 166:5448-5455.

Huang, J., et al., "TCR-Mediated Internalization of Peptide-MHC Complexes Acquired by T Cells," Science 1999; 286(5441):952-954.

Iwasaki, A., et al., "Freshly Isolated Peyer's Patch, But Not Spleen, Dendritic Cells Produce Interleukin 10 and Induce the Differentiation of T Helper Type 2 Cells," J. of Experimental Med. 1999; 190(2):229-239.

Iyoda, T., et al., "The Cd8+ Dendritic Cell Subset Selectively Endocytoses Dying Cells in Culture and In Vivo," J. Exp. Med. 2002; 195(10):1289-1302.

Jeannin, P., et al., "OmpA targets dendritic cells, induces their maturation and delivers antigen into the MHC class I presentation pathway," Nature Immunol. 2000; 1(6):502-509.

Johansson-Lindbom, B., et al., "Selective Generation of Gut Tropic T Cells in Gut-associated Lymphoid Tissue (GALT): Requirement for GALT Dendritic Cells and Adjuvant," J. Exp. Med. 2003; 198(6):963-969.

Leenen, P.J.M., et al., "Heterogeneity of Mouse Spleen Dendritic Cells: In Vivo Phagocytic Activity, Expression of Macrophage Markers, and Subpopulation Turnover," J. of Immunol. 1998; 160:2166-2173.

Lees, A., et al., "Rapid Stimulation of Large Specific Antibody Responses with Conjugates of Antigen and Anti-IgD Antibody," J. of Immunol. 1990; 145(11):3594-3600.

Lehnert, K., et al., "MAdCAM-1 costimulates T cell proliferation exclusively through integrin $\alpha^4\beta_7$, whereas VCAM-1 and CS-1 peptide use $\alpha^4\beta_1$: evidence for "remote" costimulation and induction of hyperresponsiveness to B7 molecules," Eur. J. Immunol. 1998; 28:3605-3615.

Li, M., et al., "Cell-Associated Ovalbumin Is Cross-Presented Much More Efficiently than Soluble Ovalbumin In Vivo," J. of Immunol. 2001; 166:6099-6103.

Martin, P., et al., "Concept of lymphoid versus myeloid dendritic cell lineages revisited: both CD8α and CD8α+ dendritic cells are generated from CD4$^{low}$ lymphoid-committed precursors," Blood 2000; 96(7):2511-2519.

Meckelein, B., et al., "Contribution of Serum Immunoglobulin Transudate to the Antibody Immune Status of Murine Intestinal Secretions: Influence of Different Sampling Procedures," Clin. Diag. Lab. Immunol. 2003; 10(5): 831-834.

Nakache, M., et al., "The mucosal vascular addressin is a tissue-specific endothelial cell adhesion molecule for circulating lymphocytes," Nature 1989; 337:179-181.

Patel, D.M., et al., "Class II MHC/Peptide Complexes Are Released from APC and Are Acquired by T Cell Responders During Specific Antigen Recognition," J. of Immunol. 1999; 163:5201-5210.

Pooley, J.L., et al., "Cutting Edge: Intravenous Soluble Antigen Is Presented to CD4 T Cells by CD8− Dendritic Cells, but Cross-Presented to CD8 T Cells by CD8+ Dendritic Cells," J. of Immunol. 2001; 166:5327-5330.

Rasmussen, I.B., et al., "The principle of delivery of T cell epitopes to antigen-presenting cells applied to peptides from influenza virus, ovalbumin, and hen egg lysozyme: Implications for peptide vaccination," PNAS 2001; 98(18): 10296-10301.

Sato, A., et al., "CD11b+ Peyer's Patch Dendritic Cells Secrete IL-6 and Induce IgA Secretion from Naive B Cells," J. of Immunol. 2003; 171:3684-3690.

Schön, M.P., et al., "Mucosal T Lymphocyte Numbers Are Selectively Reduced in Integrin $\alpha_E$ (CD103)—Deficient Mice," J. of Immunol. 1999; 162:6641-6649.

Schulz, O., et al., "Cross-presentation of cell-associated antigens by CD8α+ dendritic cells is attributable to their ability to internalize dead cells," Immunology 2002; 107:183-189.

Skea, D.L., et al., "Studies of the Adjuvant-Independent Antibody Response to Immunotargeting," J. of Immunol. 1993; 151(7):3557-3567.

Shortman, K., et al, "Mouse and Human Dendritic Cell Subtypes," Nature Reviews 2002; 2:151-161.

Stagg, A.J., et al., "Intestinal dendritic cells increase T cell expression of α4β7 integrin," Eur. J. Immunol. 2002; 32:1445-1454.

Tiisala, S., et al., "$\alpha_E\beta_7$ and $\beta_4\beta_7$ integrins associated with intraepithelial and mucosal homing, are expressed on microphages," Eur. J. Immunol. 1995; 25:411-417.

Uhlemann, A., et al., "Stimulation of TK1 Lymphoma Cells via $\alpha_4\beta_7$ Integrin Results in Activation of src-Tyrosine- and MAP-Kinases," Biochem. Biophys. Res. Comm. 1997; 239:68-73.

Vremec, D., et al., "CD4 and CD8 Expression by Dendritic Cell Subtypes in Mouse Thymus and Spleen," J. of Immunol. 2000; 164:2978-2986.

Wang, H., et al., "Rapid antibody responses by low-dose, single-step, dendritic cell-targeted immunization," PNAS 2000; 96(2):847-852.

You, Z., et al., "Targeting Dendritic Cells to Enhance DNA Vaccine Potency," Cancer Res. 2001; 61:3704-3711.

Yrlid, U., et al., "Antigen Presentation Capacity and Cytokine Production by Murine Splenic Dendritic Cell Subsets upon *Salmonella* Encounter," J. of Immunol. 2002; 169: 108-116.

Adams, G.P., et al., "Generating improved single-chain Fv molecules for tumor targeting," J. Immunol. Methods 1999; 231:249-260.

Boder, E.T., et al., "Yeast surface display for screening combinatorial polypeptide libraries," Nature Biotech. 1997; 15:553-557.

Burton, D.R., "Phage display," Immunotechnology 1995; 1:87-95.
Cardoso, A.I., et al., "Immunization with Plasmid DNA Encoding for the Measles Virus Hemagglutinin and Nucleoprotein Leads to Humoral and Cell-Mediated Immunity," Virology 1996; 225:293-299.
Conry, R.M., et al., "Immune Response to a Carcinoembryonic Antigen Polynucleotide Vaccine," Cancer Res. 1994; 54:1164-1168.
Cox, G.J., et al., "Bovine Herpesvirus 1: Immune Responses in Mice and Cattle Injected with Plasmid DNA," J. Virol. 1993; 67(9):5664-5667.
Cwirla, S.E., et al., "Peptides on phage: A vast library of peptides for identifying ligands," Proc. Natl. Acad. Sci. USA 1990; 87:6378-6382.
Davis, H.L., et al., "DNA-based immunization induces continuous secretion of hepatitis B surface antigen and high levels of circulating antibody," Human Molecular Genetics 1993; 2(11):1847-1851.
Deliyannis, G., et al., "A fusion DNA vaccine that targets antigen-presenting cells increases protection from viral challenge," PNAS 2000; 97(12):6676-6680.
Donnelly, J.J., et al., "Immunization with DNA," J. Immunol. Methods 1994; 176:145-152.
Dubree, N.J.P., et al., "Selective α4β7 Integrin Antagonists and Their Potential as Antiinflammatory Agents," J. Med. Chem. 2002; 45:3451-3457.
Fynan, E.F., et al., "DNA vaccines: Protective immunizations by parenteral, mucosal, and gene-gun inoculations," Proc. Natl. Acad. Sci. USA 1993; 90:11478-11482.
Hudson, P.J., et al., "High avidity scFv multimers; diabodies and triabodies," J. Immunol. Methods 1999; 231:177-189.
Lee, C.K., "Vaccination Against *Helicobacter pylori* in Non-Human Primate Models and Humans," Scand. J. Immunol. 2001; 53:437-442.
Lunde, E., et al., "Efficient Delivery of T Cell Epitopes to APC by Use of MHC Class II-Specific Troybodies," J. of Immunol. 2002; 168:2154-2162.
Neutra, M.R., et al., "Antigen Sampling Across Epithelial Barriers and Induction of Mucosal Immune Responses," Annu. Rev. Immunol. 1996; 14:275-300.

Pfeifer, A., et al., "Gene Therapy: Promises and Problems," Annu. Rev. Genomics Hum. Genet. 2001; 2:177-211.
Raag, R., et al., "Single-chain Fvs," FASEB J. 1995; 9:73-80.
Scott, J.K., et. al., "Searching for Peptide Ligands with an Epitope Library," Science, New Series 1990; 249(4967):386-390.
Sedegah, M., et al., "Protection against malaria by immunization with plasmid DNA encoding circumsporozoite protein," Proc. Nati. Acad. Sci. USA 1994; 91:9866-9870.
Smith, A.M., et al., "Phase I/II Study of G17-DT, an Anti-Gastrin Immunogen, in Advanced Colorectal Cancer," Clin. Cancer Res. 2000; 6:4719-4724.
Wang, B., et al., "Gene inoculation generates immune responses against human immunodeficiency virus type 1," Proc. Natl. Acad. Sci. USA 1993; 90:4156-4160.
Ulmer, J.B., et al., "Heterologous Protection Against Influenza by Injection of DNA Encoding a Viral Protein," Science, New Series 1993; 259(5102):1745-1749.
Van Ginkel, F.W., et al., "Vaccines for mucosal immunity to combat emerging infectious diseases," Emer. Inf. Dis. 2000; 6(2):123-133.
Watson, S.A., et al., "Antiserum Raised against an Epitope of the Cholecystokinin B/Gastrin Receptor Inhibits Hepatic Invasion of a Human Colon Tumor," Cancer Res. 2000; 60:5902-5907.
Wolff, J.A., et al., "Conditions Affecting Direct Gene Transfer into Rodent Muscle In Vivo," BioTechniques 1991; 11(4):474-485.
Xiang, Z.Q., et al., "Vaccination with a Plasmid Vector Carrying the Rabies Virus Glycoprotein Gene Induces Protective Immunity against Rabies Virus," Virology 1994; 199:132-140.
Yang, K., et al., "Early studies on DNA-based immunizations for measles virus," Vaccine 1997; 15(8):888-892.
Savinov et al J. Exp. Med. vol. 197 No. 5 Mar. 3, 2003 pp. 643-656.
Herzenberg et al Clinical Chemistry vol. 48 No. 10 pp. 1819-1827, (2002).
Quiding-Jarbrink et al Gut 2001, vol. 49 pp. 519-525.
Reiter et al 1997 Proc Natl Acad Sci USA vol. 94 pp. 4631-4636.
McKenzie et al Oct. 2004 International Immunology vol. 16 No. 11 pp. 1613-1622.
Skea et al 1993 Journal of Immunology vol. 151 pp. 3557-3568.

* cited by examiner

RELAY VACCINE

FIELD OF THE INVENTION

The present invention relates to a targeted vaccine strategy. In particular the present invention relates to a vaccination strategy where the antigen is targeted to lymphocytes which carry the antigen to MAdCAM⁺ mucosal lymphoid tissues.

BACKGROUND OF THE INVENTION

DCs are the centre-piece of the immune system. They orchestrate the type and intensity of the immune mechanisms that prevent disease. Given the heterogeneity of these immune mechanisms, it is not surprising that the DC subsets that control them are equally diverse. From the first description of DCs as antigen presenting cells [1], there has been a concerted effort to categorise the phenotypically distinct subsets and ascribe functional differences. Such studies unveiled that DCs could be divided into subsets by their expression of CD8 into CD8⁺, CD8$^{int}$ (intermediated expression) and CD8⁻ populations [2-4]. The CD8⁻ populations can be further divided into CD4⁻CD8⁻ (double negative DN) and CD4⁺CD8⁻ populations [5, 6]. Segregation of DCs by these markers has uncovered significant differences in anatomical localization [7-9], antigen uptake and processing [10, 11] as well as cytokine production [12-15]. Although maturation/activation states of the subset, as well as the nature and amount of the antigen encountered can play a large role in dictating the functional outcome, some functional ascriptions have been made. For example, it is believed that CD8⁺ DCs (found mainly in the T-cell areas) are preferentially involved in cross-priming CTL responses [16-18], whereas CD8⁻ DCs (mainly found in non T-cell areas) may be more associated with potentiating T helper type 2 [17] and B-cell responses [7, 9].

Along with phenotypic distinctions associated with the expression of CD8, the origin of the DCs can have significant impact on the induction of cytokine as well as T and B-cell responses. This is particularly evident when comparing DCs isolated from mucosal versus peripheral tissues. For example, DCs isolated from Peyer's Patches stimulate the production of more IL-4 and IL-10 but less IFN-γ [19]. In fact these IL-4 and IL-10 inducing cells are far more potent in stimulating allogenic T-cell proliferation compared with splenic DCs [19]. CD11b+ CD8− DCs isolated from the Peyer's Patches also preferentially secrete IL-6 and induce the secretion of IgA from naïve B-cells [20]. DCs from the mesenteric lymph nodes preferentially enhance T-cell expression of the mucosal homing receptor LPAM-1 as well as chemokine receptor CCR9 [21, 22].

Targeting DCs via non-lineage specific cell surface markers such as, MHC class II [23], CD11c [24], CD80/CD86 [25], toll-like receptors [26], DEC205 [27] and immunoglobulin Fc-receptors [28, 29], can enhance the systemic response to antigen. These strategies however, fail to deliver antigen at the levels required for the induction of mucosal immunity. One approach to mucosal vaccination attempted to target M-cells (in gut lining) that shuttle antigen from the mucosal surface to underlying lymphoid tissue [30, 31]. Although somewhat promising, these techniques have so far failed to overcome the problems faced in effectively delivering antigens for the efficient induction of mucosal immune responses.

To combat the constant threat of infection, the mucosa is littered with a diverse assortment of specialised lymphocyte populations. Positioning of these lymphocytes throughout the mucosa is critical for proper effector function. Thus, lymphocyte positioning is tightly regulated by the coordination of a number of unique homing receptors. These include the specific expression of cellular adhesion molecules VCAM-1, ICAM-1, MAdCAM-1 and E-cadherin. Lymphocytes use heterodimeric complexes of the integrin family such as $\alpha_4\beta_7$ (LPAM-1) [32-34], $\alpha_4\beta_1$ (LPAM-2) [35], and $\alpha_E\beta_7$ [36, 37] to bind to these adhesins and move through the tissue in search of antigen presenting DCs. Once lymphocytes encounter DCs, they form close interactions that are required for antigen recognition. Indeed, these interactions are so close that the DC can acquire membrane components (including bound antigens) from the lymphocyte [38-40]. It is therefore possible that lymphocyte populations programmed with unique and well-characterised homing potentials could be used as carriers to deliver antigen to particular DC populations. Such a mechanism may overcome the lack of suitable markers for the efficient delivery of vaccine antigens to mucosal DCs and may overcome the normal barriers to the induction mucosal IgA responses.

Given that DCs are constantly bombarded with lymphocytes that do express unique homing receptors, the present inventors have proposed a 2-step targeting model whereby lymphocytes could "relay" antigen to sites of immune induction. The mucosal homing receptor lymphocyte Peyer's Patch adhesion molecule-1 (LPAM) was investigated. LPAM is upregulated on mucosally targeted lymphocytes where it facilitates the interaction with the mucosal address in cellular adhesion molecule-1 (MAdCAM) [32, 41]. The present inventors provide a model for lymphocyte mediated delivery of antigen to mucosal lymphoid tissues of the gut as well as to peripheral lymphoid tissues.

SUMMARY OF THE INVENTION

In a first aspect, the present invention provides a method of raising an immune response in an animal, the method comprising administering to the animal a composition comprising a carrier and an antigen bound to a targeting moiety, wherein the targeting moiety binds to at least one receptor, the receptor being characterised in that it is upregulated on lymphocytes that home to MAdCAM⁺ mucosal lymphoid tissues.

In a second aspect, the present invention provides a targeted antigen comprising an antigen bound to a targeting moiety wherein the targeting moiety binds to at least one receptor, the receptor being characterised in that it is upregulated on lymphocytes that home to MAdCAM⁺ mucosal lymphoid tissues.

In a third aspect, the present invention provides an antigenic composition, the composition comprising a carrier and an antigen bound to a targeting moiety wherein the targeting moiety binds to at least one receptor, the receptor being characterised in that it is upregulated on lymphocytes that home to MAdCAM⁺ mucosal lymphoid tissues.

In a fourth aspect, the present invention provides a method of raising an immune response in an animal, the method comprising administering to the animal a composition comprising a carrier and an isolated nucleic acid molecule, the nucleic acid molecule encoding an antigen and a targeting moiety which binds to at least one receptor, the receptor being characterised in that it is upregulated on lymphocytes that home to MAdCAM⁺ mucosal lymphoid tissues.

In a fifth aspect, the present invention provides an isolated nucleic acid molecule, the nucleic acid molecule encoding an antigen and a targeting moiety which binds to at least one receptor, the receptor being characterised in that it is upregulated on lymphocytes that home to MAdCAM⁺ mucosal lymphoid tissues.

In a sixth aspect, the present invention provides an antigenic composition, the composition comprising a carrier and art isolated nucleic acid molecule, the nucleic acid molecule encoding an antigen and a targeting moiety which binds to at least one receptor, the receptor being characterised in that it is upregulated on lymphocytes that home to MAdCAM$^+$ mucosal lymphoid tissues.

DETAILED DESCRIPTION OF THE INVENTION

Figure 1:
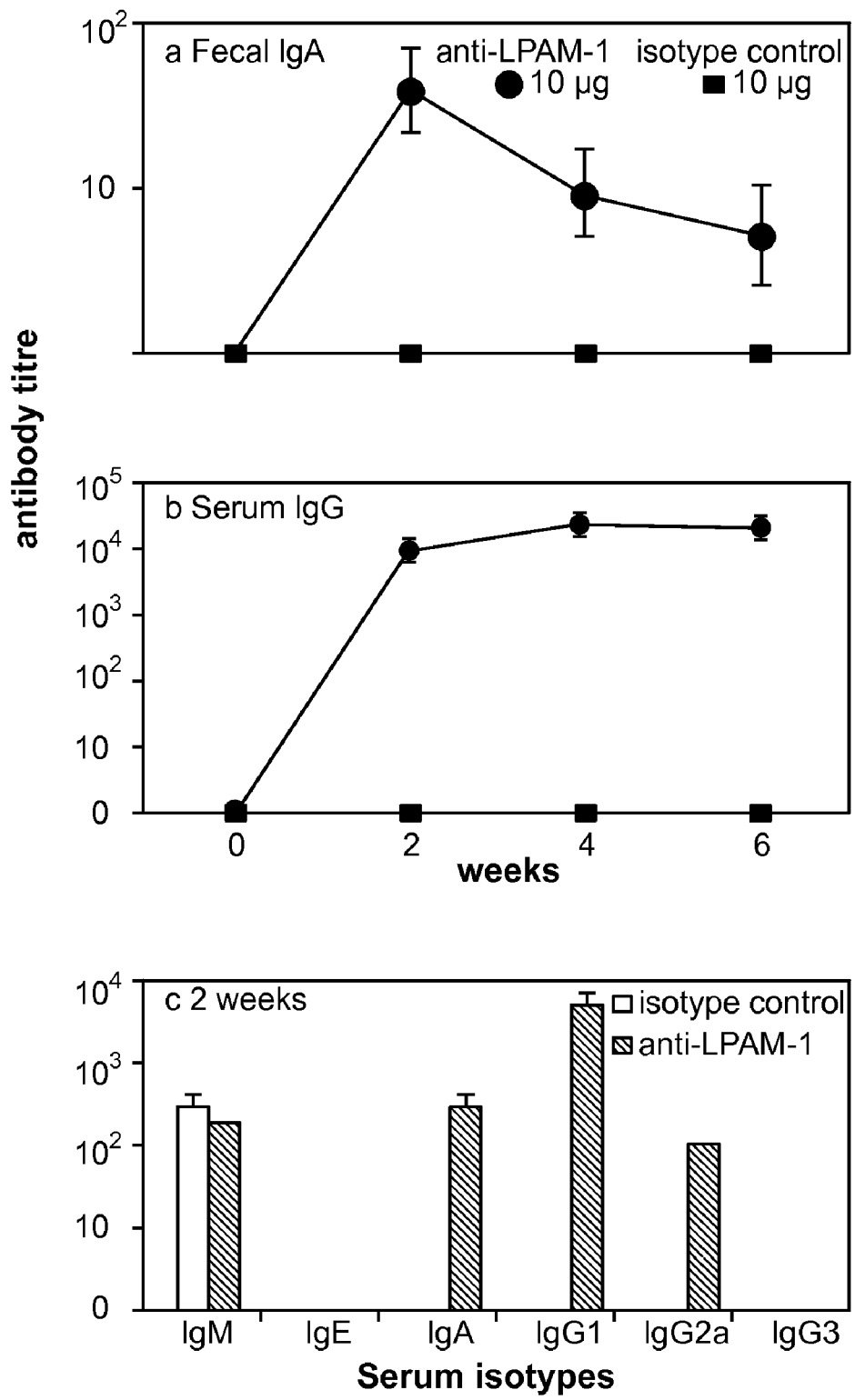
FIG. 1. Targeting LPAM enhances mucosal and systemic antibody responses in a dose dependent manner. Mice were immunized intravenously with 10 μg is of either anti-LPAM mAb DATK32 or the rat IgG2a isotype control GL117 in 0.2 ml of saline. Rat IgG2a specific Ab responses for fecal IgA (a) and serum IgG (b) were measured by ELISA at 0, 2, 4 and 6 weeks. 2 weeks after immunization IgM, IgE and IgA as well as IgG subclass (IgG1, IgG2a and IgG3) anti-rat IgG2a responses in serum were measured by ELISA (a). Means±SE are shown.

The present inventors have identified a unique relay approach to antigen targeting that substantially improves mucosal and systemic antibody responses.

In a first aspect, the present invention provides a method of raising an immune response in an animal, the method comprising administering to the animal a composition comprising a carrier and an antigen bound to a targeting moiety, wherein the targeting moiety binds to at least one receptor, the receptor being characterised in that it is upregulated on lymphocytes that home to MAdCAM$^+$ mucosal lymphoid tissues.

In a second aspect, the present invention provides a targeted antigen comprising an antigen bound to a targeting moiety wherein the targeting moiety binds to at least one receptor, the receptor being characterised in that it is upregulated on lymphocytes that home to MAdCAM$^+$ mucosal lymphoid tissues.

In a preferred embodiment of the present invention, the targeting moiety binds to a receptor which is a member of the integrin family. More preferably, the receptor is the mucosal horning receptor lymphocyte Peyer's Patch adhesion molecule (LPAM). Still more preferably, the receptor is $\alpha_4\beta_7$ integrin (LPAM-1).

LPAM facilities the interaction with the mucosal addressin cellular adhesion molecule-1 (MAdCAM) [32, 41] present in mucosal lymphoid tissue. LPAM-1$^{high}$ lymphocytes are targeted to mucosal lymphoid tissue through their specific interaction with the mucosal homing receptor MAdCAM-1. Accordingly, such lymphocytes provide a mechanism for "relaying" antigen to sites of immune induction.

In a third aspect, the present invention provides an antigenic composition, the composition comprising a carrier and an antigen bound to a targeting moiety wherein the targeting moiety binds to a receptor, the receptor being characterised in that it is upregulated on lymphocytes that home to MAdCAM$^+$ mucosal lymphoid tissues.

In a preferred embodiment of the third aspect of the invention, the composition is administered to the animal parenterally. Various routes of administration may be employed including intravenous (IV), intramuscular (IM), intraperitoneal (IP), subcutaneous (SC) and intradermal (ID). It is preferred that the administration is by a hematogenous route.

In a fourth aspect, the present invention provides a method of raising an immune response in an animal, the method comprising administering to the animal a composition comprising a carrier and an isolated nucleic acid molecule, the nucleic acid molecule encoding an antigen and a targeting moiety which binds to a receptor, the receptor being characterised in that it is upregulated on lymphocytes that home to MAdCAM+ mucosal lymphoid tissues.

In a fifth aspect, the present invention provides an isolated nucleic acid molecule, the nucleic acid molecule encoding an antigen and a targeting moiety which binds to a receptor, the receptor being characterised in that it is upregulated on lymphocytes that home to MAdCAM+ mucosal lymphoid tissues.

In a sixth aspect, the present invention provides an antigenic composition, the composition comprising a carrier and an isolated nucleic acid molecule, the nucleic acid molecule encoding an antigen and a targeting moiety which binds to a receptor, the receptor being characterised in that it is upregulated on lymphocytes that home to MAdCAM+ mucosal lymphoid tissues.

Preferably, the nucleic acid molecule according to the fourth, fifth and sixth aspects is a DNA molecule. More preferably, it is a cDNA.

In a preferred embodiment of the fourth, fifth and sixth aspect, the targeting moiety binds a receptor which is a member of the integrin family. More preferably, the receptor is the mucosal homing receptor lymphocyte Peyer's Patch adhesion molecule (LPAM). Still more preferably, the receptor is $\alpha_4\beta_7$ integrin. (LPAM-1).

Molecules which target LPAM are known in the art, for example the LPAM specific rat IgG2a monoclonal antibody DATK32 which is commercially available. It is presently preferred that the targeting moiety is an antibody, an antibody fragment or an antibody binding domain. Further information regarding antibody fragments such as single chain Fvs can be found in, for example, Hudson P J & Kortt A A. "High avidity scFv multimers; diabodies and triabodies". J. Immunol. Meth. 231 (1999) 177-189; Adams G P & Schier R. "Generating improved single-chain Fv molecules for tumor targeting". J. Immunol. Meth. 231 (1999) 249-260; Raag R & Whitlow M. "Single-chain Fvs" FASEB J. 9 (1995) 73-80; Owens R J & Young R J. "The genetic engineering of monoclonal antibodies". J. Immunol. Meth. 168 (1994) 149-165.

Additional ligands that target LPAM-1 and adhesins may be generated by using peptide display libraries such as those made in phage display technology (Burton D R. "Phage display. Immununotechnology." 1995 1:87-94; Cwirla S E, Peters E A, Barrett R W, Dower W J. Peptides on phage: a vast library of peptides for identifying ligands. Proc Natl. Acad Sci USA. 1990 87:6378-82; Scott J K, Smith G P. "Searching for peptide ligands with an epitope library." Science. 1990 249:386-90; Dubree et al, J Med Chem, 45:3451) as well as peptide libraries displayed on other surface components e.g. on flagella molecules (Westerlund-Wikstrom B. "Peptide display on bacterial flagella: principles and applications." Int J Med Microbiol. 2000 290:223-30) or on yeast (Boder E T, Wittrup K D. "Yeast surface display for screening combinatorial polypeptide libraries." Nat. Biotechnol. 1997 15:553-7).

As will be recognised by those skilled in the field of protein chemistry there are numerous methods by which the antigen may be bound to the targeting moiety. Examples of such methods include:

1) affinity conjugation such as antigen-ligand fusions where the ligand has an affinity for the targeting antibody (examples of such ligands would be streptococcal protein G, staphylococcal protein A, peptostreptococcal protein L) or bispecific antibody to cross-link antigen to targeting moiety.
2) chemical cross-linking. There are a host of well known cross-linking methods including periodate-borohydride, carbodiimide, glutaraldehyde, photoaffinity labelling, oxirane and various succinimide esters such as maleimidobenzoyl-succinimide ester. Many of these are readily available commercially e.g. from Pierce, Rockford, Ill., USA. There are many references to cross-linking techniques including Hermanson G T "Bioconjugate Techniques" Academic Press, San Diego 1996; Lee Y C, Lee R T. Conjugation of glycopeptides to proteins. Methods Enzymol. 1989; 179:253-7; Wong S S "Chemistry of Protein Conjugation and Cross-linking" CRC Press 1991; Harlow B & Lane D "Antibodies: A Laboratory Manual" Cold Spring Harbor Laboratory, 1988; Marriott G, Ott J. Synthesis and applications of heterobifunctional photocleavable cross-linking reagents. Methods Enzymol. 1998; 291:155-75.
3) genetic fusions. These can be made as recombinant antibody-antigen fusion proteins (in bacteria, yeast, insect or mammalian systems) or used for DNA immunization with or without spacers between the antibody and antigen. There are many publications of immunoglobulin fusions to other molecules. Fusions to antigens like influenza hemagglutinin are known in the art see, for example, Deliyannis G, Boyle J S, Brady J L, Brown L E, Lew A M. "A fusion DNA vaccine that targets antigen-presenting cells increases protection from viral challenge." Proc Natl Acad Sci USA. 2000 97:6676-80. Short sequences can also be inserted into the immunoglobulin molecule itself [Lunde E, Western K H, Rasmussen I B, Sandlie I, Bogen B. "Efficient delivery of T cell epitopes to APC by use of MHC class II-specific Troybodies." J Immunol. 2002 168:2154-62]. Shortened versions of antibody molecules (e.g. Fv fragments) may also be used to make genetic fusions [Reiter Y, Pastan I. "Antibody engineering of recombinant Fv immunotoxins for improved targeting of cancer: disulfide-stabilized Fv immunotoxins." Clin Cancer Res. 1996 2:245-52].

As will be understood by persons skilled in the art, whatever the method of targeting moiety-antigen fusion used, such fusions need to be able to target the receptor, such as LPAM-1, in vivo. It is therefore highly preferable that binding of the targeting moiety-antigen fusion to cells other than mucosal homing lymphocytes is minimised. Furthermore, antigens which have a high propensity for binding to cells or tissues other than mucosal homing lymphocytes and/or cells or tissues on route to mucosal lymphoid tissues should also be avoided. This can be tested in vitro for example by determining whether the targeting moiety-antigen fusion non-specifically bind to cryostat sections of the mucosal tissue by immunohistology.

The antigen used in the present invention can be any antigen against which it is desired to raise an immune response. It is preferred that the antigen is selected such that an immune response is generated against any pathogen whose main portal of entry is the gut and those that colonise mucosal surface. This would include *Salmonella, Cholera, Helicobacter pylori*, rectally introduced HIV, *Candida, P. gingivalis*, gut parasites or gut associated toxins. Moreover, the present invention may be used to induce an immune response to gut hormones (e.g. gastrin) or their receptors for gut associated cancers [Watson S A, Clarke P A, Morris T M, Caplin M E. "Antiserum raised against an epitope of the cholecystokinin B/gastrin receptor inhibits hepatic invasion of a human colon tumor." Cancer Res. 2000 60:5902-7; Smith A M, Justin T, Michaeli D, Watson S A. "Phase I/II study of G17-DT, an anti-gastrin immunogen, in advanced colorectal cancer." Clin Cancer Res. 2000 6:4719-24].

Information regarding HIV antigens such as gp120 and other candidates can be found in Stott J, Hu S L, Almond N.

"Candidate vaccines protect macaques against primate immunodeficiency viruses." AIDS Res Hum Retroviruses. 1998 Oct.; 14 Suppl 3:S265-70.

Information regarding *Helicobacter pylori* antigens such as urease of *Helicobacter pylori* and other candidates can be found in Lee C K. "Vaccination against *Helicobacter pylori* in non-human primate models and humans." Scand J Immunol. 2001 May; 53(5):437-42.

In addition, the antigen may be derived from intimin which is the ligand by which enteropathogenic *Escherichia coli* cells adhere to gut epithelial cells causing haemorrhagic enteritis.

Further information regarding antigens in which mucosal immunity is important may be found in van Ginkel F W, Nguyen H H, McGhee J R. "Vaccines for mucosal immunity to combat emerging infectious diseases." Emerg Infect Dis. 2000 March-April; 6(2):123-32; and Neutra M R, Pringault E, Kraehenbuhl J P. "Antigen sampling across epithelial barriers and induction of mucosal immune responses." Annu Rev Immunol. 1996; 14:275-300.

As will be recognised by those skilled in the art, the fourth to sixth aspects of the present invention relate to DNA vaccination.

The ability of direct injection of non-replicating plasmid DNA coding for viral proteins to elicit protective immune responses in laboratory and preclinical models has created increasing interest in DNA immunisation. A useful review of DNA vaccination is provided in Donnelly et al, Journal of Immunological Methods 176 (1994) 145-152, the disclosure of which is incorporated herein by reference.

DNA vaccination involves the direct in vivo introduction of DNA encoding an antigen into tissues of a subject for expression of the antigen by the cells of the subject's tissue. DNA vaccines are described in U.S. Pat. Nos. 5,939,400, 6,110,898, WO 95/20660 and WO 93/19183, the disclosures of which are hereby incorporated by reference in their entireties. The ability of directly injected DNA that encodes an antigen to elicit a protective immune response has been demonstrated in numerous experimental systems (see, for example, Conry et al., Cancer Res 54:1164-1168, 1994; Cardoso et al, Immuniz Virol 225:293-299, 1996; Cox et a L, J Virol 67:5664-5667, 1993; Davis et al, Hum Mol Genet 2:1847-1851, 1993; Sedegah et al, Proc Natl Acad. Sci. USA 91:9866-9870, 1994; Montgomery et al., DNA Cell Biol 12:777-783, 1993; Ulmer et al, Science 259:1745-1749, 1993; Wang et al., Proc Natl Acad Set USA 90:4156-4160, 1993; Xiang eta, Virology 199:132-140, 1994; Yang et al., Vaccine 15:888-891, 1997; Ulmer eta, Science 259:1745, 1993; Wolff et al Biotechniques 11:474, 1991).

To date, most DNA vaccines in mammalian systems have relied upon viral promoters derived from cytomegalovirus (CMV). These have had good efficiency in both muscle and skin inoculation in a number of mammalian species. A factor known to affect the immune response elicited by DNA immunization is the method of DNA delivery, for example, parenteral routes can yield low rates of gene transfer and produce considerable variability of gene expression (Montgomery et al., DNA Cell Biol12:777-783, 1993). High-velocity inoculation of plasmids, using a gene-gun, enhanced the immune responses of mice (Fynan et al., Proc Natl Acad Sci USA 90:11478-11482, 1993; Eisenbraun et al., DNA Cell Biol 12:791-797, 1993), presumably because of a greater efficiency of DNA transfection and more effective antigen presentation by dendritic cells. Vectors containing the nucleic acid-based vaccine of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter.

Additionally, other modes of delivery of DNA vaccines may be contemplated including the use of viral vectors via retrovirus or adenovirus mediated transduction of target cells (such as reviewed in Alexander Pfeifer and Inder M Verma. Annual Review of Genomics and Human Genetics. Vol 2:177-211 "Gene Therapy: Promises and Problems" (2001).

Alternatively, bacteriophage mediated DNA transfer may be employed. Suitable bacteriophage vectors include M13 bacteriophage, f1 bacteriophage, lambda bacteriophage, P1 bacterlophage, SP6 bacteriophage, T3 bacteriophage, T7 bacteriophage and ØX174 bacteriophage.

Suitable carriers for use in the present invention will be familiar to those skilled in the art, such as for example phosphate buffered saline.

As used herein the term "animal" encompasses both human and non-human animals.

As used herein the term "mucosal lymphoid tissue" encompasses tissue that is associated with mucosal surfaces and is referred to as mucosa associated lymphoid tissue (MALT) of the gut, respiratory tract and genital tract. It has commonly been called GALT or gut-associated lymphoid tissue when associated with the alimentary tract.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in the specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood preferred forms thereof will be described with reference to the following Examples.

Materials and Methods

Immunisations

The rat IgG2a mAb immunogens used were an anti-LPAM mAb DATK32, a rat IgG2a isotype control (GL117 that recognizes bacterial β-galactosidase), an anti-intraepithelial lymphocyte (IEL) mAb M290, an anti-$\alpha_4$ integrin mAb MFR4.B and an anti-$\beta_7$ integrin mAb FIB27. These mAbs were purchased from Pharmingen (San Diego, Calif., USA) or isolated from hybridoma supernatants and purified on immobilized protein G (Amersham Pharmacia Biotech, Little Chalfont, UK). CBA mice (6-8 wk old female; 5 per group unless otherwise stated) were used for all experiments. Oral immunizations were performed by gavage in 3% wt/vol sodium bicarbonate buffer after light anaesthesia with methoxyflurane (Medical developments, Springvale, Australia). For co-immunization and OT-II proliferation experiments ovalbumin (OVA) grade V (Sigma. St Louis, Mo., USA) was dissolved in PBS and mixed with targeting or control mAbs. All immunogens contained less than 0.06 ng of endotoxin per mg of Ag, as determined by the *Limulus* Amebocyte Lysate assay (Kinetic-QCL, BioWhittaker, Walkersville, Md.)

Preparation of DNA Vaccine

Large-scale isolation of DNA for immunization studies was performed using an alkaline lysis/triton X-114 method.

Transformed DH5α E. coli were grown to saturation overnight in 100 ml of superbroth containing 100 μg/ml of ampicillin at 37° C. 50 ml of starting cultures was then transferred to 600 ml of superbroth containing 100 μg/ml of ampicillin and grown at 37° C. for 24 hours. After centrifugation at 3000 g the pelleted bacteria were fully resuspended in a total of 40 ml of solution i (25 mM Tris-HCl pH=8, 10 mM EDTA pH8.0, 15% sucrose). 100 ml of fresh solution II (10 ml 2M NaOH, 85 $H_2O$, 5 ml 20% SDS) was added before incubation on ice for 10 min. 75 ml of cold solution III (5 M potassium acetate pH5) was then mixed by inversion and left on ice for 30 min. After centrifugation at 10000 g; 30 min, 4° C., supernatant was filtered through 2 layers of kimwipes (Kimberley-Clarke, NSW, Aust) and 0.6 volume of isopropanol added to precipitate DNA. DNA was then resuspended in 5 ml of TE (10 mMtris, 1 mM EDTA pH=8) with 20 mg/ml of DNAse-free RNAse (Promega, Madison, Wis., USA), and placed at 37"C for 30 min. Equal volume of polyethylene glycol (13% PEG 8000 in 1.6M NaCl) was added and left at 4° C. overnight before centrifugation at 4000 g for 20 min. DNA pellet was resuspended in 9.5 ml TE and 0.5 ml of 3 M sodium acetate pH8.9 and phenol/chloroform extractions performed 3 times followed by a chloroform only extraction. DNA was precipitated by the addition of equal volumes of isopropanol and centrifugation at 4000 g. Pellet was then resuspended in 10 ml of MTPBS and 100 μl of tritonX-114 added to remove endotoxin. Solution was thoroughly mixed and placed on ice for 4 min until clear. Solution was then placed at 40° C. for 5 min then centrifuged at 3000 g for 5 min to pellet tritonX-114-endotoxin. TritonX114 endotoxin extractions were repeated 3 times in total. DNA was then precipitated with equal volume of isopropanol and stored at 4° C. for after resuspension in normal saline Preparation of Fecal Samples for Analysis of Gut IgA Responses Mucosal Ab isolated from fecal samples was used as a measure of gastrointestinal immune responses [42]. Briefly, 1 ml of 0.1 mg/ml soybean trypsin inhibitor (Sigma Chemical Co, St Louis, Mo., USA) in PBS was added per 0.1 g of faeces then vortexed in a mini-beadbeater (Biospec Products, Bartlesville, Okla., USA) for 10 s at 2500 rpm, debris removed by centrifugation 9000 g, 4° C., for 15 min, and supernatant assayed for Ab.

ELISA

Rat IgG2a, and OVA specific Ab responses from serum, fecal and culture supernatant samples were determined by ELISA. Briefly, microtiter plates (Dynatech, Chantilly, Va., USA) coated with Ag (2 μg/ml in PBS) were incubated with serially diluted sera, fecal extract, or culture supernatant (diluted in blocking buffer of 5% skim-milk powder in PBS) overnight at 4° C. Bound Ab was detected after 3 hr incubation at room temp with peroxidase-conjugated antibodies to mouse IgG (donkey anti-mouse, adsorbed against rat Ig; Chemicon, Temecula, Calif.), IgA, IgM, IgE (goat anti-mouse), IgG1, IgG2a, IgG2b, or IgG3 (rat anti-mouse) (Southern Biotechnology, Birmingham, Ala.) diluted in blocking buffer. The substrate used was tetramethyl-benzidine (TMS, Sigma Chemical Co, St Louis, Mo., USA) in 0.1 M sodium acetate pH 6 and reactions stopped with 0.5 M sulphuric acid. IgG and IgA titres were defined as the reciprocal of the highest dilution to reach an $OD_{450\ nm}$ of 0.1.

ELISPOT

To determine the number of cells secreting Ab, ELISPOT assays were performed. Briefly, 96 well sterile multiscreen filtration plates (Millipore S. A. Yvelines, Cedex, France) coated with rat IgG2a (GL117, 20 μg/ml in PBS) were incubated for 36 hr at 37° C. 10% $CO_2$ with dilutions of single cell lymphocyte preparations isolated from mesenteric lymph nodes (MLN), Foyers Patch (PP), inguinal lymph nodes (ILN) or spleen. Bound Ab was detected after incubation with peroxidase-conjugated antibodies to mouse IgA (Southern Biotechnology, Birmingham, Ala., USA) diluted in blocking buffer. Numbers of spots representing individual Ag specific ASC were counted under a stereo microscope after development with AEC substrate (Dako Co, Carpinteria, Calif., USA).

Lymphocyte Cell Culture

Lymphocyte cell culture was used to reinforce ELISPOT data. Lymphocytes were prepared as described (see ELISPOT) and cultured for 5 days in 96 well plates in 0.2 ml of RPMI 10% FCS, 37° C., 10% $CO_2$. Supernatants were then removed and assayed for antigen specific IgG and IgA responses by ELISA.

In-Vivo OT-II Proliferation Assay

Carboxyfluorescein diacetate, succinimidyl ester (CFSE) labelling of OVA specific TCR transgenic CD4+ T-cells (OT-II) cells was performed as previously described [43]. Briefly, OT-II T-cells were resuspended in PBS containing 0.1% BSA (Sigma, St. Louis, Mo.) at $10^7$ cells/ml. For fluorescence labelling, 2 μl of a CFSE (Molecular Probes, Eugene, Oreg.) stock solution (5 mM in DMSO) was incubated with $10^7$ cells for 10 min. at 37° C. C57/B16 mice were primed with either OVA alone, or OVA mixed with various doses of anti-LPAM mAb DATK32. Three days after priming mice were sacrificed and single cell suspensions made from ILN and MLN. CD4+ T-cells were then stained in FACS buffer (PBS, 5% FCS, 2.5 mM EDTA) with anti-CD4-PE (Caltag, Burlingame, Calif., USA) and proliferation of CFSE+ PE+ T-cells was measured by sequential loss of CFSE by flow cytometric analysis using a FACScan (Becton Dickinson, Mountain View, Calif.).

In-Vivo Lymphocyte Homing Assay

CFSE labelling of MLN cells was performed as described above. Labelled cells were then mixed with various doses of anti-LPAM (DATK32) or isotype control (GL117) mAbs and immediately injected intravenously. 3 hr after, mice were sacrificed and single cell suspensions made from ILN and MLN and homing of CFSE+ cells from the blood analysed by flow cytometric analysis using a FACScan (Becton Dickinson, Mountain View, Calif.).

While Blood Cell Analysis

Total whiteblood cells counts were performed using a Coulter-counter (Beckman Coulter, Miami, Fla., USA). For analysis of lymphocyte subsets, red blood cells were first lysed from whole blood then remaining cells stained in FACS buffer with fluorescent labelled Ab against mouse CD4, CD8 and B220. Cells were then washed twice and analysed by flow cytometric analysis using a FACScan (Becton Dickinson, Mountain View, Calif.).

Results

Targeting the Mucosal Lymphocyte Homing Receptor LPAM Enhances Gut Mucosal IgA Responses to a Model Antigen To investigate the influence of LPAM ($\alpha_4\beta_7$ integrin) targeting on mucosal Ab responses the rat IgG2a anti-mouse LPAM mAb DATK32 was employed as a model targeted antigen. Isotypic differences between rat and mouse IgC renders rat IgG2a immunogenic in mice. Thus, anti-rat IgG2a responses can be measured to this targeted antigen and compared to other non-targeted rat IgG2a mAbs (in this case the anti-bacterial (3-galactosidase mAb GL117 that has no known reactivity in the mouse). To analyze mucosal responses in the gut, the fecal extract technique was used that allows for non-invasive monitoring of responses with minimum contamination from serum immunoglobulins [44]. Remarkably it was found that gut mucosal responses could be significantly enhanced by targeting LPAM in this model (FIG. 1a). Gut mucosal response could be induced after parenteral immunization with as little as 10 µg of LPAM-targeted antigen (FIG. 1a). Moreover, these could be induced in the absence of any additional adjuvants normally required to stimulate mucosal responses (FIG. 1a). Mucosal IgA responses peaked 2 weeks after immunization were still present 6 weeks after a single immunization (FIG. 1a). In contrast to this, immunization with the non-targeted isotype control failed to induce a detectable response (FIG. 1a).

LPAM-Targeting Enhances Systemic Ab Responses

With significant enhancements in gastrointestinal IgA responses after LPAM-targeting, the inventors then investigated the influence of targeting on the systemic Ab response. Following the finding in the gut mucosal compartment, LPAM-targeting lead to significant improvements in the systemic Ab response (FIG. 1b). Parenteral targeting of LPAM with as little as 10 µg of mAb, stimulated a significant anti-rat IgG2a IgG response in the serum (FIG. 1b). In fact, the systemic IgG response was approximately 10,000 fold higher than that of the non-targeted control (FIG. 1b). Like the mucosal response, serum IgG responses appeared rapidly, being detected as early as 2 weeks after a single immunization. However, unlike mucosal responses, serum IgG response remained around their elevated peak long after 2 weeks (FIG. 1b).

With the different immunoglobulin isotypes possessing different protective effects, it was important to consider the influence of LPAM-targeting on the Ab subclass response. Despite a remarkable enhancement in total systemic IgG responses, no difference was found in early IgM responses (FIG. 1c). The IgM response was not influenced by antigen targeting or antigen dose (FIG. 1c). Similarly, the IgE responses were not influenced by antigen targeting or dose, with no detectable responses induced (FIG. 1c). However, serum IgA anti-rat IgG2a responses were influenced by antigen targeting and dose (FIG. 1c). Immunization with 10 µg of LPAM-targeted antigen led to enhancements in both the IgG1 and IgG2a subclass response (FIG. 1c). Serum IgG3 responses could not be detected in any animals (FIG. 1c).

Figure 2:
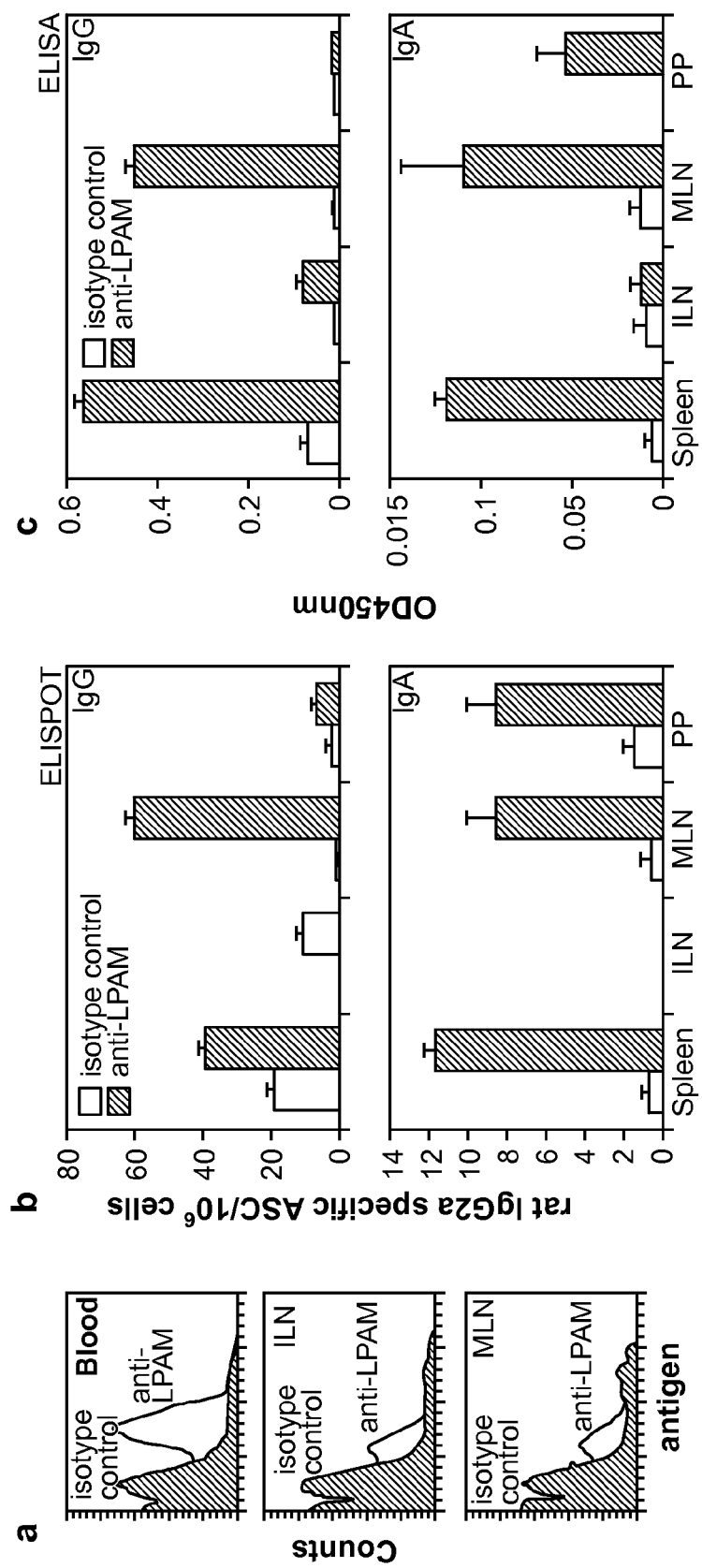
FIG. 2. LPAM-targeting localizes antigen to peripheral and mucosal tissues to enhance systemic and mucosal IgA and IgG production. (a) Mice were immunized intravenously with 100 μg of either anti-LPAM mAb DATK32 or the isotype control GL117. 1 hr after, blood, ILN, and MLN were harvested and lymphocytes stained for antigen with PE-conjugated anti-rat Ig and analysed by FACS. (b) Mice were immunized intravenously with 10 μg of either anti-LPAM mAb DATK32 or the isotype control GL117. 11 d after, spleen, ILN, MLN and PP were harvested and assayed for rat IgG2a specific IgA and IgG Ab secreting cells (ASC) by ELISPOT; Means±SE (spots/10$^6$ cells) are shown. (c) Mice were immunized intravenously with 10 μg of either anti-LPAM mAb DATK32 or the isotype control GL117. 11 d after, spleen, ILN, MLN and PP cells were harvested cultured for 5 days and supernatant assayed for rat IgG2a specific IgA and IgG Ab by ELISA. Means±SE of OD 450 ma are shown.

LPAM-Targeting Localizes Antigen to Mucosal and Peripheral Lymphoid Tissue In-Vivo To investigate the in-vivo localization of intravenously delivered anti-LPAM mAb, both FACS and immunohistological based techniques were employed. The anti-LPAM mAb DATK32 does not recognize its ligand in immunohistology (Pharmingen, unpublished results). These findings were confirmed due to a failure to detect binding to LPAM on lymph node sections stained via intravenous injection or ex-vivo incubation (data not shown). As a result it was decided to move to the FACS based assay that measured mAb binding to surface LPAM. Consistent with the reported expression of LPAM [45], it was found that intravenous injection of this mAb stained the majority of circulating blood lymphocytes (FIG. 2a). More importantly parenteral LPAM-targeting lead to preferential localization of antigen within both the peripheral (ILN) and mucosal (MLN) compartments (FIG. 2a).

Enhanced Ab responses induced by LPAM-targeting is the result of improved IgA and IgC Production from Both Mucosal and Peripheral Lymphoid Compartments Given the substantial increase in Ab responses induced by LPAM-targeting the inventors wanted to investigate the origin of these enhancements. To achieve this ELISPOT and lymphocyte culture assays were performed to evaluate IgG and IgA responses within the mucosal and peripheral lymphoid compartments. Consistent with the analysis of serum and fecal Ab responses, LPAM-targeting enhanced the IgG and IgA response in both mucosal and systemic tissues (FIGS. 2b&c). Elevated IgA responses could be detected from cells in the MLN and PP (FIGS. 2b&c), characteristic of local gut mucosal responses. Although IgA responses could not be detected in the ILN, the centerpiece of peripheral lymphoid machinery, the spleen, contributed remarkably to the IgA response (FIGS. 2b&c). Taken together these findings are consistent with the enhanced mucosal and systemic IgA responses induced by LPAM-targeting. Similarly, IgG response were enhanced in both the mucosal and systemic compartments (FIGS. 2b&c). Targeting significantly elevated IgG responses in both the spleen and ILN (FIGS. 2b&c). Although we failed to detect improvements in IgG responses from PP cells, the MLN contributed significantly to these responses (FIGS. 2b&c). Overall, ELISPOT and lymphocyte culture assays were consistent with our previous findings revealing significant improvements in IgG and IgA responses in peripheral and mucosal responses.

Figure 3:
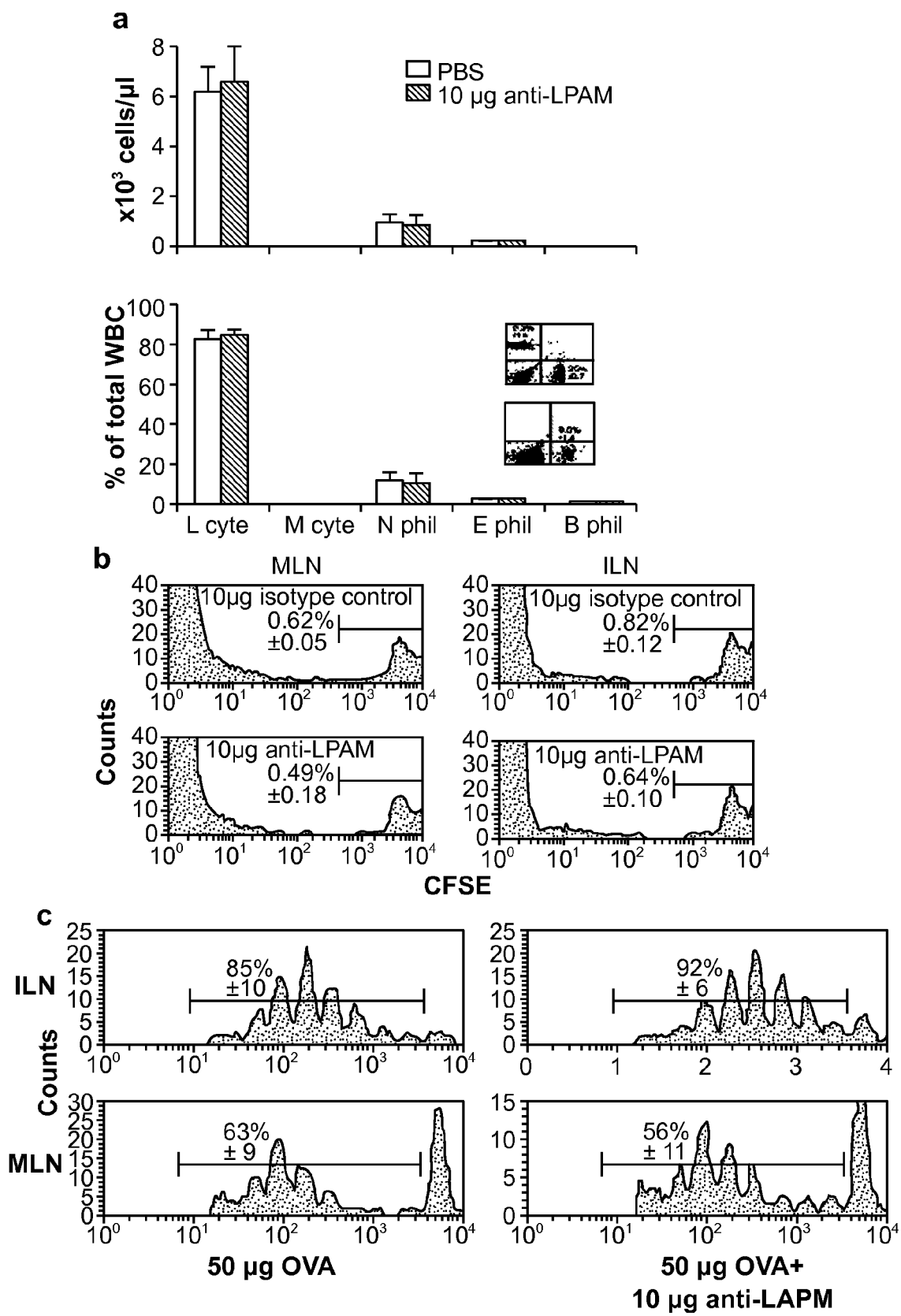
FIG. 3. Immunizing daces of anti-LPAM mAbs do not deplete target populations, inhibit homing or alter antigen specific proliferation of CD4+ T-cells in-vivo. (a) Mice were immunized intravenously with either 10 μg of anti-LPAM mAb DATK32 in 0.2 ml of PBS or a PBS only control. 1 day after, white blood cell (WBC) percentages and total cell numbers were analysed from the blood using a coulter-counter. CD4$^+$, CD8$^+$ and B220$^+$ lymphocyte proportions were analysed by FACS (inlay of bottom panel in a). (b) Mice received an intravenous injection of 5×10$^6$ CFSE labelled MLN cells mixed with 10 μg of either anti-LPAM mAb DATK32 or isotype control mAb GL117 in 0.2 ml of saline. Three hr after, MLN and ILN were harvested and homing of CPSE labelled cells analysed by FACS. (c) Mice received an intravenous injection of 5×10$^6$ CFSE labelled OT-II (CD4+ class II restricted OVA specific TCR transgenic). 1 d after, mice were immunized 50 μg of OVA only or mixed with 10 μg of anti-LPAM mAb DATK32 0.2 ml of saline. Three days after, MLN and ILN were harvested and proliferation CFSE labelled OVA specific CD4+ T-cells cells analysed by FACS.

Immunizing doses of anti-LPAM mAbs do not deplete target populations, inhibit Homing or Alter Antigen Specific Proliferation of CD4+ T-Cells In-Vivo Anti-LPAM mAbs such as DATK32 can have a number of effects on LPAM$^+$ populations. For example, Abs that bind the $\alpha_4\beta_7$ integrin complex at high doses can block lymphocyte homing. It was also possible that this mAb depletes particular target cells in-vivo, influencing the Ab response. To segregate such bystander effects from that of antigen targeting, the influence of immunizing doses of anti-LPAM mAb DATK32 on normal blood cell populations, homing and T-cell activation within both the mucosal and systemic compartments was investigated. It was found that mAb DATK32 did not influence the normal numbers or proportions of white blood cells (FIG. 3a). Lymphocyte, monocyte, neutrophil, eosinophil and basophil numbers were all equivalent to animals injected with controls, suggesting that this mAb does not deplete these cells (FIG. 3a). This was extended further to show that animals immunized with anti-LPAM mAb had normal proportions of CD4$^+$ and CD8$^+$ T-cells as well as B220$^+$ B-cells in the blood (FIG. 3a inset of bottom panel). It was also found that immunizing doses of anti-LPAM mAb did not affect the homing of cells from the blood into the MLN or ILN (FIG. 3b). No significant differences in the proportion of CFSE labelled MLN cells homing back to the MLN or to the peripheral ILN was observed during administration of immunizing doses of anti-LPAM mAb (FIG. 3b).

The LPAM complex has been identified as a possible costimulatory interaction involved in T-cell activation. Natural ligands as well as mAbs can bind to LPAM promoting intracellular signalling, aggregation and activation of T-cells [35, 46]. To explore the possible costimulatory effects of this mAb the inventors employed an in-vivo model widely used for studying CD4$^+$ T-cell activation, the proliferation of CFSE labelled OVA specific class-II restricted T-cell transgenic OT-II cells. This model enabled the study of T-cell proliferation in-vivo within both the mucosal and systemic compartments. It was found that immunizing doses of anti-LPAM mAb had no influence on the proliferative response of OT-H cells to OVA (FIG. 3c). The percentage of divided and undivided cells was not significantly different if mice were immunized with OVA alone or in combination with 10 µg of the anti-LPAM mAb (FIG. 3c).

Targeting to LPAM is Required for Enhanced Mucosal IgA Responses

Figure 4:
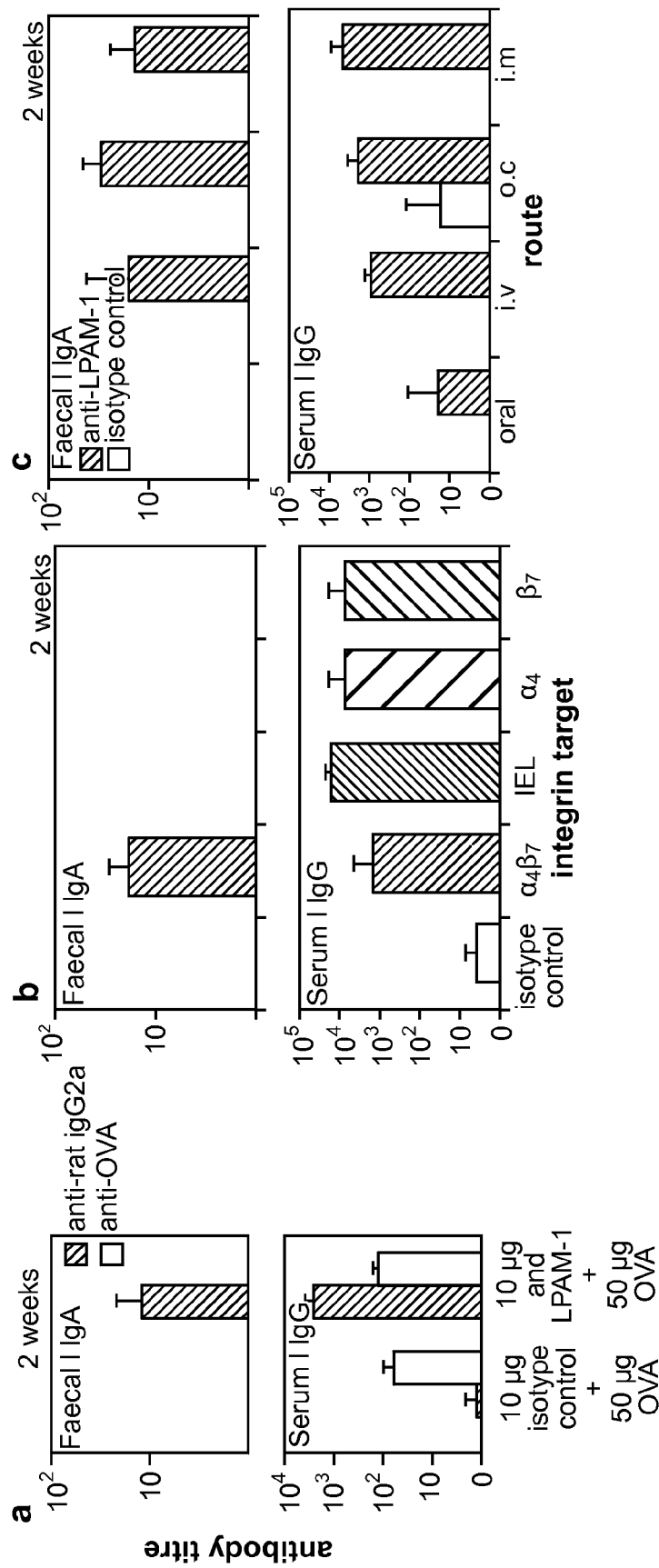
FIG. 4. Enhanced responses induced by anti-LPAM require targeting but not intravenous delivery. (a) Mice were immunized intravenously with 10 μg of either anti-LPAM mAb DATK32 or isotype control mAb GL117 mixed with 50 μg of ovalbumin (OVA) in 0.3 ml of saline. OVA and rat IgG2a specific Ab responses for fecal IgA and serum IgG were measured by ELISA at 2 wk. (b) Mice were immunized intravenously with 10 μg of either anti-$\alpha_4\beta_7$ (LPAM) mAb DATK32, isotype control mAb GL117, anti-intraepithelial lymphocyte (IEL) mAb M290, anti-$\alpha_4$ integrin mAb MPR4.B or the anti-$\beta_7$ integrin mAb FTB27. Rat IgG2a specific Ab responses for fecal IgA and serum JgG were measured by ELISA at 2 wk. (c) Mice were immunized orally, intravenously, subcutaneously or intramuscularly with 10 μg of either anti-LPAM mAb DATK32 or the isotype control mAb GL117. Rat IgG2a specific Ab responses for fecal IgA and serum IgG were measured by ELISA at 2 wk.

As well as T-cells, LPAM ligands such as mAbs could directly influence B-cell responses. To further dissect possible bystander effects from that of antigen targeting, co-immunization experiments were performed. Animals received the anti-LPAM mAb DATK32 or the non-targeted isotype control GL117 mixed with 50 µg of OVA. Two weeks after immunization, fecal and serum samples were collected and IgG and IgA responses were measured against rat IgG2a as well as OVA. It was found that targeting with anti-LPAM mAb DATK32, had no effect on the anti OVA response (FIG. 4a). Anti-OVA serum IgG was equivalent in both the LPAM-targeted and non-targeted groups (FIG. 4a). Furthermore, co-immunization of OVA with anti-LPAM mAb did not result in the induction of anti-OVA fecal IgA responses (FIG. 4a). Co-immunization of OVA with the mAb had no effect on the anti-rat IgG responses in the mucosal or systemic compartments (FIG. 4a). Taken together these data argue against the involvement of bystander effects of anti-LPAM mAbs in the induction of improved systemic and mucosal Ab responses. Moreover, it shows that targeting of antigen to LPAM is required for the observed effects.

The inventors wanted to further analyse the requirement for antigen targeting in the induction of mucosal and systemic responses within their model. To achieve this, mice were immunized with other rat IgG2a mAb antigens including those recognizing mucosal intraepithelial lymphocytes (IEL) as well as the individual components of the LPAM complex ($\alpha_4$ and $\beta_7$ integrins). As $\alpha_4$ and $\beta_7$ pair with other molecules (e.g. $\beta_1$ and $\alpha_E$ respectively), it would be expected that mAb to these components would not be as specific as the anti-LPAM in mAb (that only recognizes the $\alpha_4\beta_7$ complex. It was found that only targeting to LPAM with DATK32 induced a fecal IgA response (FIG. 4b). Targeting TEL as well as the sub-components of LPAM failed to induce a fecal IgA response (FIG. 4b). The same effect was observed in animals immunized with up to 10 fold higher doses of anti-IEL, anti-$_4$ and anti-$_7$ (data not shown). However, targeting with anti-IEL, anti-$\alpha_4$ or anti-$\beta_7$ mAbs all enhanced the systemic response (FIG. 4b), pointing to possible avenues for future application of these targets.

LPAM-Targeting Enhances Responses after Parenteral but not Mucosal Delivery of Targeted Antigen Parenteral vaccines are usually given via subcutaneous or intramuscular routes. To investigate whether such routes could mirror the responses induced intravenously, mice were immunized intramuscularly and subcutaneously with either anti-LPAM mAb (DATK32) or non-targeted control (GL117). Importantly, these routes were found to be equally efficient in improving responses by LPAM-targeting (FIG. 4c). LPAM-targeting led to mucosal responses through the intramuscular and subcutaneous routes at similar levels to those through the intravenous route (FIG. 4c). Similarly, serum IgG responses remained greatly elevated and were not significantly different to intravenous immunizations (FIG. 4c). As expected, oral immunization in the absence of mucosal adjuvants failed to induce a mucosal response to either the targeted or non-targeted antigen (FIG. 4c). Targeting did however improve the systemic IgG response to orally administered antigen, however this enhancement was only modest and remained 100 fold less than responses induced by parenteral antigen targeting.

LPAM-1 Targeted DNA Immunisation

Figure 5:
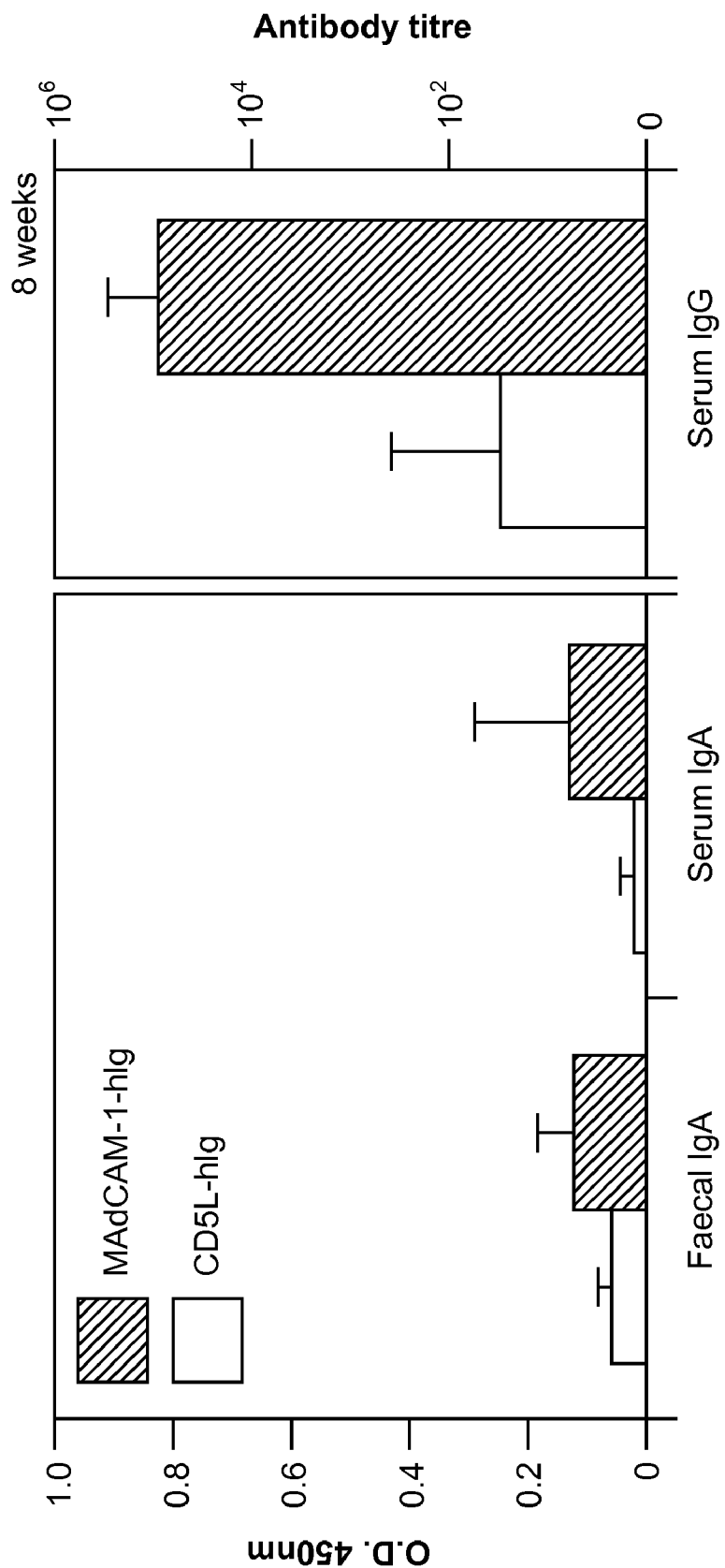
FIG. 5. An LPAM-1 targeted DNA vaccine augments systemic Ab responses. Mice (5 per group) were immunised intramuscularly with 200 μg of plasmid encoding either LPAM-1 targeted MAdCAM-1-hIg or non-targeted CD5 leader (CD5L)-hIg (expresses the human Ig only) at 0 and 6 weeks. Human IgG specific faecal IgA, serum IgA and serum IgG Ab responses were measured by ELISA at 8 weeks. Means±SD of O.D. 450 nm are shown for faecal IgA (1:10 dilution of faecal sample) and serum IgA (1:50 dilution of scrum). Means±SD log Ab titres are shown for serum IgG response.

A DNA immunisation strategy was employed to investigate the ability of LPAM-1 targeted antigen to enhance mucosal and systemic immune responses. Mice were immunised intramuscularly with either a non-targeted or LPAM-1 targeted DNA vaccine. LPAM-1 targeting was achieved through fusion of human Ig antigen to the extracellular region of MAdCAM-1. It was found that LPAM-1 targeted DNA vaccination enhanced the subsequent Ab response (FIG. 5). Immunisation with either targeted or non-targeted DNA vaccine was unable to induce a significant faecal or serum IgA response (FIG. 5); it is not known whether the lack of IgA response was because not enough protein was expressed in the DNA vaccine to achieve targeting or because the affinity of MAdCAM-hIg was insufficient compared with anti-LPAM antibody. In contrast, both targeted and non-targeted DNA vaccines were able to induce significant serum IgG responses (FIG. 5). Moreover, the systemic Ab induced by LPAM-1 targeting was 10-100 fold higher than the non-targeted control immunisation (FIG. 5).

LPAM is used by naïve, activated and memory lymphocyte populations to home to MAdCAM$^+$ mucosal lymphoid tissues [32, 34, 45, 47]. Blocking this interaction with either anti-MAdCAM or anti-LPAM mAb inhibits the homing of mucosal lymphocytes [33, 48]. Given the high levels of expression of LPAM along with its unique role in directing lymphocytes to mucosal tissues, it was proposed that it may be an ideal target for systemic delivery of mucosally targeted vaccines. Targeting antigen to this specialized lymphocyte population may direct antigen to mucosal inductive tissue in a 2 step or "relay" fashion. Therefore a protein immunization model using a rat IgG2a anti-mouse LPAM mAb DATK32 was chosen, whereby the mAb serves as both immunogen and targeting moiety. Remarkably, it was found that targeting LPAM with DATK32 induced a potent mucosal and systemic response. Systemic responses were greatly enhanced, and importantly, targeted protein immunization enabled sufficient localization of antigen to the mucosal associated lymphoid tissue for induction of mucosal Ab responses.

Closer investigation of the Ab response to LPAM-targeting immunizations revealed several interesting findings. Although targeting did not improve the IgM or IgE response, IgA, IgG1 and IgG2a responses were significantly enhanced. Elevated IgA, IgG1 and IgG2a responses are consistent with enhancements in both Th1 and Th2 type responses. ELISPOT and lymphocyte culture assays showed that elevated serum IgG responses were the result of improved production from both mucosal and systemic tissues. These responses are consistent with the localisation of targeted antigen to these sites. Interestingly, the same pattern emerged when the origin of IgA responses were investigated. Elevated serum and fecal IgA responses were associated with IgA responses in peripheral and mucosal tissues. In fact the IgA responses in the spleen were remarkable and equally as potent as those induced in mucosal tissues that normally dominate the IgA response. It remains to be elucidated whether splenic IgA responses were dependent on the traffic of DCs from mucosal tissues or whether IgA responses were primed at this site by a presentation mechanism skewed towards IgA production. Given the potency of this response, it is suggested that the later may be more likely. Overall, it is clear that LPAM-targeting results in enhanced Ab responses by stimulating production across a number of lymphoid sites.

The inventors found no differences in the total numbers or proportions of white blood cells in mice treated with anti-LPAM. In fact, lymphocyte homing, T-cell activation and the induction of Ab response against a co-injected antigen in either the mucosal and systemic compartments were not different in animals that received anti-LPAM mAb. From these results it was concluded that bystander effects are unlikely to contribute. Importantly, these studies also revealed that IgA and IgG responses induced by anti-LPAM mAb are not the result of aberrant homing, T-cell proliferative or B-cell responses and are mostly likely resultant of antigen localization to LPAM. This was reinforced by the finding that targeting intraepithelial lymphocytes or the separate components of LPAM ($\alpha_4$ and $\beta_7$ integrin individually; these molecules can pair with other molecules found in other cells) failed to induce a mucosal response. Although the enhanced systemic IgG responses that were induced warrant further investigation, this data further illustrates that LPAM-targeting is required for mucosal IgA responses.

Route of administration is an important consideration in the development of novel vaccine strategies. This is particularly salient for vaccines aimed at inducing mucosal responses as such responses are rarely induced to parenterally delivery vaccines. Direct mucosal administration provides a better chance of reaching the specialized lymphoid tissues that governs protection of these sites; however, adjuvants are almost always required to overcome the biases that maintain tolerance or non-responsiveness to the heavy burden of harmless antigens. Mucosal IgA responses could however, be induced by delivery of LPAM-targeted antigen by traditional parenteral routes (subcutaneous and intramuscular). This reinforced the findings using the intravenous route and highlights a layer of flexibility that may be important in the future clinical application of this technology.

Although the highest expression of LPAM can be found in mucosal lymphocytes, a high proportion of peripheral lymphocytes also express low to intermediate levels [33, 49]. For example, 30% of the total lymphocyte population in the spleen express LPAM [33]. This was illustrated in the localisation studies by a large proportion of LPAM$^+$ cells staining for antigen in the blood, ILN as well as the MLN. It is likely that the localisation of antigen to both the systemic and mucosal compartments underlies the improved Ab responses. However, it is not clear which population of lymphocytes is responsible for this effect. Interestingly, this is not the first report of enhanced Ab responses induced by targeting antigen to specialized populations of lymphocytes. An early study of the immunotargeting approach by Skea, et al, (1993), reported that Ab responses could be enhanced by targeting T cells [50]. They found that targeting antigen to CD3$^+$ and CD4$^+$ lymphocytes via specific mAb, enhanced the subsequent Ab response [50]. They failed to elucidate any of the underlying mechanisms of this enhancement but proposed that B cell binding to antigen coated T cells may focus T cell help and promote antigen specific B cell responses. A similar mechanism may also function in the LPAM-targeting model. This group also reported enhance Ab responses by targeting CD45RA that is predominantly expressed on B cells [50]. Other groups have also reported similar effects [51, 52] which have been attributed to the antigen presenting function of targeted B cells [53]. As B cells express LPAM through various stages of maturation [45, 47], B cell targeting may also play a role in enhanced responses to LPAM-targeted antigen. To add further complexity, LPAM expression is not limited to lymphocyte populations. For instance, although blood monocytes are LPAM, they dramatically upregulate LPAM after activation with IFN-γ [54]. The importance of targeting various cell populations for enhanced responses remains to be elucidated and highlights an important avenue for future experiments.

In conclusion, the present study provide a model and proof of principle that targeting lymphocytes in an antigen relay approach to vaccination can improve antigen specific responses. Most importantly this approach facilitated the induction of mucosal IgA responses not normally induced to parenteral vaccines. Furthermore, induction of mucosal IgA was associated with a marked elevation of systemic responses. Further characterization of the LPAM-targeting model, for example dissecting the mechanisms of antigen transfer, may lead to further improvements in the induction of mucosal and systemic immune responses.

DNA immunisation with the LPAM-1 targeted antigen resulted in greatly enhanced systemic Ab responses. However, this strategy was unable to significantly enhance the faecal or serum IgA response. Assuming that localisation of LPAM-1 targeted antigen follows its predominant expression on mucosal lymphocytes, the dichotomy noted between the mucosal and systemic Ab responses to DNA immunisation may reflect a lower antigenic threshold required for induction of systemic immune responses.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Steinman R M, Cohn Z A. Identification of a novel cell type in peripheral lymphoid organs of mice. I. Morphology, quantitation, tissue distribution. J Exp Med 1973; 137(5): 1142-62.
2. Wu L, Li C L, Shortman K. Thymic dendritic cell precursors: relationship to the T lymphocyte lineage and phenotype of the dendritic cell progeny. J Exp Med 1996; 184(3):903-11.
3. Martin P, del Hoyo G M, Anluere F, Ruiz S R, Arias C P, Marin A R, et al. Concept of lymphoid versus myeloid dendritic cell lineages revisited: both CD8alpha(−) and CD8alpha(+) dendritic cells are generated from CD4(low) lymphoid-committed precursors. Blood 2000; 96(7):2511-9.
4. Anjuere F, Marlin P, Ferrero I, Fraga M L, del Hoyo G M, Wright N, et al. Definition of dendritic cell subpopulations present in the spleen, Peyer's patches, lymph nodes, and skin of the mouse. Blood 1999; 93(2):590-8.
5. Vremec D, Pooley J, Hochrein H, Wu L, Shortman K. CD4 and CD8 expression by dendritic cell subtypes in mouse thymus and spleen. J Immunol 2000; 164(6):2978-86.
6. Shortman K, Liu Y J. Mouse and human dendritic cell subtypes. Nat Rev Immunol 2002; 2(3):151-61.
7. Balazs M, Martin r, Zhou T, Kearney J. Blood dendritic cells interact with splenic marginal zone B cells to initiate T-independent immune responses. Immunity 2002; 17(3): 341-52.
8. Leenen P J, Radosevic K, Voerman J S, Salomon B, van Rooijen N, Klatzmann D, al. Heterogeneity of mouse spleen dendritic cells: in vivo phagocytic activity, expression of macrophage markers, and subpopulation turnover. J Immunol 1998; 160(5):2166-73.
9. Garcia De Vinuesa C, Gulbranson-Judge A, Khan M, O'Leary P, Cascalho M, Wabl M, et al. Dendritic cells associated with plasmablast survival. Eur J Immunol 1999; 29(11):3712-21.
10. Schulz O, Reis e Sousa C. Cross-presentation of cell-associated antigens by CD8alpha+ dendritic cells is attributable to their ability to internalize dead cells. Immunology 2002; 107(2):183-9.
11. Iyoda T, Shimoyaina S, Liu K, Omatsu Y, Akiyarna Y, Maeda Y, et al. The CD8+ dendritic cell subset selectively endocytoses dying cells in culture and in vivo. J Exp Med 2002; 195(10):1289-302.
12. Hochrein I I, Shortman K, Vremec D, Scott B, Hertzog P, O'Keeffe M. Differential production of IL-12, IFN-alpha, and IFN-gamma by mouse dendritic cell subsets. J Immunol 2001; 166(9):5448-55.

13. Boonstra A, Asselin-Paturel C, Gilliet M, Crain C, Trinchieri G, Liu Y J, et al. Flexibility of mouse classical and plasmacytoid-derived dendritic cells in directing T helper type 1 and 2 cell development: dependency on antigen dose and differential toll-like receptor ligation. J Exp Med 2003; 197(1):101-9.
14. Asselin-Paturel C, Boonstra A, Dalod M, Durand I, Yessaad N, Dezutter-Dambuyant C, et al. Mouse type I IFN-producing cells are immature APCs with plasmacytoid morphology. Nat Immunol 2001; 2(12):1144-50.
15. Yrlid U, Wick M J. Antigen presentation capacity and cytokine production by murine splenic dendritic cell subsets upon *Salmonella* encounter. J Immunol 2002; 169(1): 108-16.
16. den Haan J M, Lehar S M, Bevan M J. CD8(+) but not CD8(−) dendritic cells cross-prime cytotoxic T cells in vivo. J Exp Med 2000; 192(12):1685-96.
17. Pooley J L, Heath W R, Shortman K. Cutting edge: intravenous soluble antigen is presented to CD4 T cells by CD8− dendritic cells, but cross-presented to CD8 T cells by CD8+ dendritic cells. J Immunol 2001; 166(9):5327-30.
18. Belz G T, Smith C M, Eichner D, Shortman K, Karupiah G, Carbone F R, et al. Cutting Edge: Conventional CD8alpha(+) Dendritic Cells Are Generally Involved in Priming CTL Immunity to Viruses. J Immunol 2004; 172 (4):1996-2000.
19. Iwasaki A, Kelsall B L. Freshly isolated Peyer's patch, but not spleen, dendritic cells produce interleukin 10 and induce the differentiation of T helper type 2 cells. J Exp Med 1999; 190(2):229-39.
20. Sato A, Hashiguchi M, Toda E, Iwasaki A, Hachimura S, Kaminogawa S. CD11b+ Peyer's patch dendritic cells secrete IL-6 and induce IgA secretion from naive B cells. J Immunol 2003; 171(7):3684-90.
21. Stagg A J, Kamm M A, Knight S C. Intestinal dendritic cells increase T cell expression of alpha4beta7 Integrin. Eur J Immunol 2002; 32(5):1445-54.
22. Johansson-Lindbom B, Svensson M, Wurbel M A, Malissen B, Marquez C, Agace W. Selective generation of gut tropic T cells in gut-associated lymphoid tissue (GALT): requirement for GALT dendritic cells and adjuvant. J Exp Med 2003; 198(6):963-9. Epub 2003 Sep. 8.
23. Carayanniotis C, Barber B H. Adjuvant-free IgG responses induced with antigen coupled to antibodies against class II MHC. Nature 1987; 327(611.7):59-61.
24. Wang H, Griffiths M N, Burton D R, Ghazal P. Rapid antibody responses by low-dose, single-step, dendritic cell-targeted immunization. Proc Natl Acad Sci USA 2000; 97(2):847-52.
25. Boyle J S, Brady J L, Lew A M. Enhanced responses to a DNA vaccine encoding a fusion antigen that is directed to sites of immune induction. Nature 1998; 392(6674):408-11.
26. Jeannin P, Renno T, Goetsch L, Miconnet I, Aubry J P, Delneste Y, et al. OmpA targets dendritic cells, induces their maturation and delivers antigen into the MHC class I presentation pathway. Nat Immunol 2000; 1(6):502-9.
27. I Tawiger D, Inaba K, Dorsett Y, Guo M, Mahnkc K, Rivera M, et al. Dendritic cells induce peripheral T cell unresponsiveness under steady state conditions in vivo. J. Exp. Med. 2001; 194(6):769-79.
28. You Z, Huang X, Hester J, Toh H C, Chen S Y. Targeting dendritic culls to enhance disease DNA vaccine potency. Cancer Res 2001; 61(9):3704-11.
29. Heijnen I A, van Vugt M J, Fanger N A, Graziano R F, de Wit T P, Hofhuis F M, et al. Antigen targeting to myeloid-specific human Fc gamma RI/CD64 triggers enhanced antibody responses in transgenic mice. J Clin Invest 1996; 97(2):331-8.
30. Frey A, Neutra M R. Targeting of mucosal vaccines to Peyer's patch M cells. Behring Inst Mitt 1997(98):376-89.
31. Foster N, Clark M A, Jepson M A, Hirst B H. *Ulex europaeus* 1 lectin targets microspheres to mouse Peyer's patch M-cells in vivo. Vaccine 1998; 16(5):536-41.
32. Berlin C, Berg E L, Briskin M J, Andrew D P, Kilshaw P J, Holzmann B, et al. Alpha 4 beta 7 integrin mediates lymphocyte binding to the mucosal vascular addressin MAdCAM-1. Cell 1993; 74(1):185-5.
33. Andrew D P, Berlin C, Honda S, Yoshino T, Hamann A, Holzmann B, et al. Distinct but overlapping epitopes are involved in alpha 4 beta 7-mediated adhesion to vascular cell adhesion molecule-1, mucosal addressin-1, fibronectin, and lymphocyte aggregation. J Immunol 1994; 153(9): 3847-61.
34. Erle D J, Briskin M J, Butcher E C, Garcia-Pardo A, Lazarovits A I, Tidswell M. Expression and function of the MAdCAM-1 receptor, integrin alpha 4 beta 7, on human leukocytes. J Immunol 1994; 153(2):517-28.
35. Lehnert K, Print C G, Yang Y, Krissansen G W. MAdCAM-1 costimulates T cell proliferation exclusively through integrin alpha4beta7, whereas VCAM-1 and CS-1 peptide use alpha4beta1: evidence for "remote" costimulation and Induction of hyperresponsiveness to B7 molecules. Eur J Immunol 1998; 28(11):3605-15.
36. Schon M P, Arya A, Murphy E A, Adams C M, Strauch U G, Agace W W, et al. Mucosal T lymphocyte numbers are selectively reduced in integrin alpha E (CD103)-deficient mice. J Immunol 1999; 162(11):6641-9.
37. Cepek K L, Shaw S K, Parker C M, Russell G J, Morrow J S, Rimm D L, et al. Adhesion between epithelial cells and T lymphocytes mediated by E-cadherin and the alpha E beta 7 integrin. Nature 1994; 372(6502):190-3.
38. Harshyne L A, Watkins S C, Gambotto A, Barratt-Boyes S M. Dendritic cells acquire antigens from live cells for cross-presentation to CTL. J Immunol 2001; 166(6):3717-23.
39. Huang J F, Yang Y, Sepulveda H, Shi W, Hwang I, Peterson P A, et al. TCR-Mediated internalization of peptide-MHC complexes acquired by T cells. Science 1999; 286(5441): 952-4.
40. Patel D M, Arnold P Y, White G A, Nardella J P, Mannie M D. Class II MHC/peptide complexes are released from APC and are acquired by T cell responders during specific antigen recognition. J Immunol 1999; 163(10):5201-10.
41. Hamann A, Andrew D P, Jablonski-Westrich D, Holzmann B, Butcher E C. Role of alpha 4-integrins in lymphocyte homing to mucosal tissues in vivo. J Immunol 1994; 152(7):3282-93.
42. Grewal H M, Iiemuning Karlsen T, Vetvik H, C, Gjessing H K, Sommerfelt I I, et al. Measurement of specific IgA in faecal extracts and intestinal lavage fluid for monitoring of mucosal immune responses. J Immunol Methods 2000; 239(1-2):53-62.
43. Li M, Davey G M, Sutherland R M, Kurts C, Lew A M, Hirst C, et al. Cell-associated ovalbumin is cross-presented much more efficiently than soluble ovalbumin in vivo. J Immunol 2001; 166(10):6099-103.
44. Meckelein B, Externest D, Schmidt M A, Frey A. Contribution of serum immunoglobulin transudate to the antibody immune status of murine intestinal secretions: influence of different sampling procedures. Clin Diagn Lab Immunol 2003; 10(5):831-4.

45. Andrew D P, Rott L S, Kilshaw P J, Butcher E C. Distribution of alpha 4 beta 7 and alpha E beta 7 integrins on thymocytes, intestinal epithelial lymphocytes and peripheral lymphocytes. Eur J Immunol 1996; 26(4):897-905.

46. Uhlemann A C, Brenner B, Gulbins E, Linderkamp O, Lang F, Holzmann B, et al. Stimulation of TK1 lymphoma cells via alpha 4 beta 7 integrin results in activation of src-tyrosine- and MAP-kinases Identification of a murine Peyer's patch-specific lymphocyte homing receptor as an integrin molecule with an alpha chain homologous to human VLA-4 alpha Integrin alpha 4 beta 7 co-stimulation of human peripheral blond T cell proliferation Expression and function of alpha 4/beta 7 integrin on human natural killer cells Alpha 4 beta 7 integrin mediates B cell binding to fibronectin and vascular cell adhesion molecule-1. Expression and function of alpha 4 integrins on human B lymphocytes. Biochem Biophys Res Commun 1997; 239(1):68-73.

47. Farstad I N, T Ialstensen T S, Lien B, Kilshaw P J, Lazarovits A I, Brandtzaeg P, et al. Distribution of beta 7 integrins in human intestinal mucosa and organized gut-associated lymphoid tissue. Immunology 1996; 89(2):227-37.

48, Nakache M, Berg E L, Streeter P R, Butcher E C. The mucosal vascular addressin is a tissue-specific endothelial cell adhesion molecule for circulating lymphocytes. Nature 1989; 337(6203):179-81.

49. Brandtzaeg P, Farstad I N, Haraldsen G. Regional specialization in the mucosal immune system: printed cells do not always home along the same track. Immunol Today 1999; 20(6):267-77.

50. Skea D L, Barber B H. Studio of the adjuvant-independent antibody response to immunotargeting. Target structure dependence, isotype distribution, and induction of long term memory. J Immunol 1993; 151(7):3557-68.

51. Lees A, Morris S C, Thyphronitis G, Holmes J M, Inman J K, Finkelman F D. Rapid stimulation of large specific antibody responses with conjugates of antigen and anti-IgD antibody. J Immunol 1990; 145(11):3594-600.

52. Rasmussen T B, Lunde E, Michaelson T E, Bogen B, Sandlie I. The principle of delivery of T cell epitopes to antigen-presenting cells applied to peptides from influenza virus, ovalbumin, and hen egg lysozyme: implications for peptide vaccination. Proc Natl Aced Sci USA 2001; 98(18):10296-301.

53. Denis O, Latinne D, Nisol F, Bazin H. Resting B cells can act as antigen presenting cells in vivo and induce antibody responses. Int Immunol 1993; 5(1):71-8.

54. Tiisala S, Paavonen T, Renkonen R. Alpha E beta 7 and alpha 4 beta 7 integrins associated with intraepithelial and mucosal homing, are expressed on macrophages. Eur J Immunol 1995; 25(2):411-7.

The invention claimed is:

1. A method of raising an immune response, comprising: administering to an animal a composition comprising a carrier, and an isolated targeted antigen, the isolated targeted antigen comprising an antigen bound to a targeting moiety, wherein the targeting moiety is selected from the group consisting of an antibody, an antibody fragment and an antibody binding domain; and wherein the targeting moiety binds to lymphocyte Peyer's Patch adhesion molecule (LPAM) receptor on lymphocytes that home to MAdCAM$^+$mucosal lymphoid tissues; and allowing the isolated targeted antibody to home to MAdCAM+$^±$ mucosal lymphoid tissue of the animal and raise immune response; wherein the antigen is any of: (a) an antigen isolated from a pathogen selected from the group consisting of *Salmonella, Cholera, Helicobacter pylori*, HIV, *Candida, P. gingivalis, enteropathogenic Escherichia coli*, and gut parasites; (b) an antigen isolated from a cellular component, wherein the cellular component is selected from the group consisting of gut associated toxins, gut hormone, and gut hormone receptors; and (c) an antigen isolated from gut associated cancers cell; and wherein the antigen is bound to the targeting moiety by a type of binding selected from the group consisting of affinity conjugation, chemical cross-linking and genetic fusions.

2. The method according to claim 1 wherein the antibody is DATK32.

3. The method as claimed in claim 1, wherein the carrier is a phosphate buffered saline solution.

* * * * *